(12) United States Patent
Sun et al.

(10) Patent No.: US 10,563,139 B2
(45) Date of Patent: Feb. 18, 2020

(54) FLEXIBLE HYDROPROCESSING OF SLURRY HYDROCRACKING PRODUCTS

(71) Applicant: UOP LLC, Des Plaines, IL (US)

(72) Inventors: Ping Sun, Riverside, IL (US); Hans G. Lefebvre, Chicago, IL (US); Grant H. Yokomizo, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 260 days.

(21) Appl. No.: 15/675,213

(22) Filed: Aug. 11, 2017

(65) Prior Publication Data

US 2018/0119034 A1 May 3, 2018

Related U.S. Application Data (60) Provisional application No. 60/414,610, filed on Oct. 28, 2016.

(51) Int. Cl.

| | |
|---|---|
| *C10G 65/12* | (2006.01) |
| *C10G 45/16* | (2006.01) |
| *C10G 47/26* | (2006.01) |
| *B01J 8/22* | (2006.01) |
| *B01J 35/02* | (2006.01) |
| *C07C 4/06* | (2006.01) |
| *C10G 47/02* | (2006.01) |

(52) U.S. Cl.
CPC .............. *C10G 65/12* (2013.01); *C10G 45/16* (2013.01); *C10G 47/26* (2013.01); *B01J 8/22* (2013.01); *B01J 35/023* (2013.01); *B01J 2208/00796* (2013.01); *B01J 2523/00* (2013.01); *C07C 4/06* (2013.01); *C10G 47/02* (2013.01); *C10G 2300/1048* (2013.01); *C10G 2300/1074* (2013.01); *C10G 2400/02* (2013.01)

(58) Field of Classification Search
None
See application file for complete search history.

(56) References Cited

U.S. PATENT DOCUMENTS

| 3,728,249 A | 4/1973 | Antezana et al. |
|---|---|---|
| 5,968,347 A | 10/1999 | Kolodziej et al. |
| 6,328,879 B1 | 12/2001 | Kalnes |
| 6,444,116 B1 | 9/2002 | Galiasso et al. |
| 6,596,157 B2 | 7/2003 | Gupta et al. |

(Continued)

FOREIGN PATENT DOCUMENTS

| WO | 9617903 A1 | 6/1996 |
|---|---|---|
| WO | 2012135460 A2 | 10/2012 |

OTHER PUBLICATIONS

PCT Search Report for corresponding International Application No. PCT/US2017/052639 dated Dec. 7, 2017.

*Primary Examiner* — Renee Robinson
*Assistant Examiner* — Derek N Mueller
(74) *Attorney, Agent, or Firm* — Paschall & Associates, LLC; James C. Paschall (57) ABSTRACT

Processes for hydrotreating an effluent from a slurry hydrocracking process are described. Different streams are formed from the SHC effluent, and different hydroprocessing conditions are applied to the streams, e.g., more severe conditions are applied to streams which need additional hydroprocessing, while less severe conditions are applied to streams which do not need as much hydroprocessing. Common equipment is shared between different hydroprocessing steps.

20 Claims, 6 Drawing Sheets

(56) References Cited

U.S. PATENT DOCUMENTS

| | | |
|---|---|---|
| 6,623,623 B2 | 9/2003 | Kalnes |
| 7,238,274 B2 | 7/2007 | Turner |
| 8,747,653 B2 | 6/2014 | Wieber |
| 8,999,144 B2 | 4/2015 | Wieber |
| 2009/0129998 A1* | 5/2009 | Haizmann .............. C10G 65/12 422/600 |
| 2010/0200459 A1 | 8/2010 | Bhattacharya |

* cited by examiner

FLEXIBLE HYDROPROCESSING OF SLURRY HYDROCRACKING PRODUCTS

CROSS-REFERENCE TO RELATED APPLICATION

This application claims priority from Provisional Application No. 62/414,610 filed Oct. 28, 2016, the contents of which cited application are hereby incorporated by reference in its entirety.

BACKGROUND OF THE INVENTION

As the reserves of conventional crude oils decline, heavy oils must be upgraded to meet world demands. In heavy oil upgrading, heavier materials are converted to lighter fractions and most of the sulfur, nitrogen and metals must be removed. Heavy oils include materials such as petroleum crude oil, atmospheric tower bottoms products, vacuum tower bottoms products, heavy cycle oils, shale oils, coal derived liquids, crude oil residuum, topped crude oils and the heavy bituminous oils extracted from oil sands. These heavy hydrocarbon feedstocks may be generally characterized by low reactivity, high heteroatom and metal content, high coking tendency, poor susceptibility to hydrocracking and difficulties in distillation. Most residual oil feedstocks which are to be upgraded contain some level of asphaltenes which are commonly known to be heptane insoluble compounds as determined by ASTM D3279 or ASTM D6560. Asphaltenes are high molecular weight compounds containing heteroatoms which impart polarity.

Heavy oils must be upgraded in a primary upgrading unit before they can be further processed into useable products. Primary upgrading units known in the art include, but are not restricted to, coking processes, such as delayed or fluidized coking, and hydrogen addition processes such as fixed bed resid hydrotreating, ebullated bed or slurry hydrocracking (SHC).

In SHC, a three-phase mixture of heavy liquid oil feed cracks in the presence of gaseous hydrogen over solid catalyst to produce lighter products under pressure at an elevated temperature. The catalysts for SHC are typically metal sulfides derived from transition metal based precursors. Iron, molybdenum, nickel, cobalt and tungsten are among typical examples.

SHC products require hydroprocessing to be used as final products. They are generally high in heteroatom content, primarily nitrogen and sulfur, and require hydroprocessing to remove these contaminants. Commonly, aromatic ring saturation is also required to meet product specifications. To sell the product as a premium product, e.g., Euro 5 diesel or gasoline, could require extreme conditions, large catalyst volume or high activity catalysts to refine.

SHC products have a broad range of boiling points with widely varying properties. Because these products do not require the same hydroprocessing severity, e.g. pressure, temperature and residence time, typically each fraction is hydroprocessed separately. As a result, hydroprocessing units are highly expensive in terms of capital investment.

Therefore, there is strong economic incentive to integrate the hydroprocessing of different fractions having different properties, either in reduced reaction steps, or by reducing the common equipment, e.g., the fractionation section and/or the hydrogen compression system. The key benefit is significant cost savings and achieving comparable, if not improved, product properties by using an integrated hydroprocessing system.

SUMMARY OF THE INVENTION

One aspect of the invention is a process for hydrotreating an effluent from a slurry hydrocracking process. In one embodiment, the process involves separating the slurry hydrocracking effluent in a hot separator into a first liquid stream and a first vapor stream. The first vapor stream is separated in a second separator into a second liquid stream and a second vapor stream. The first and second liquid streams are fractionated into at least two fractions in a first fractionation zone, wherein the at least two fractions comprise at least a first fraction and a second fraction, the second fraction having a T5 boiling point above the T5 boiling point of the first fraction. The second fraction is hydrotreated in the presence of hydrogen and a hydrotreating catalyst in a first hydrotreating reactor to form a first hydrotreated effluent. The first hydrotreated effluent and the first fraction are hydrotreated in the presence of hydrogen and a hydrotreating catalyst in a second hydrotreating reactor to form a second hydrotreated effluent. The second hydrotreated effluent is separated into at least two fractions in a separation zone, wherein the at least two fractions comprise at least a naphtha product fraction and a diesel product fraction.

In another embodiment, the process involves separating the slurry hydrocracking effluent in a hot separator into a first liquid stream and a first vapor stream. The first liquid stream is fractionated into at least two fractions in a first fractionation zone, wherein the at least two fractions comprise at least a first fraction and a second fraction, the second fraction having a boiling point above the boiling point of the first fraction. The first fraction and at least a portion of the first vapor stream are hydrotreated in the presence of hydrogen and a hydrotreating catalyst in a first hydrotreating reactor to form a first hydrotreated effluent. The first hydrotreated effluent is separated into at least two fractions in a separation zone, wherein the at least two fractions comprise at least a naphtha product fraction and a diesel product fraction.

DETAILED DESCRIPTION OF THE INVENTION

Processes have been developed in which different streams are formed from the SHC effluent, and different hydroprocessing conditions are applied to the streams, e.g., more severe conditions are applied to streams which need additional hydroprocessing, while less severe conditions are applied to streams which need less hydroprocessing. Common equipment is shared between different hydroprocessing steps.

Figure 1:
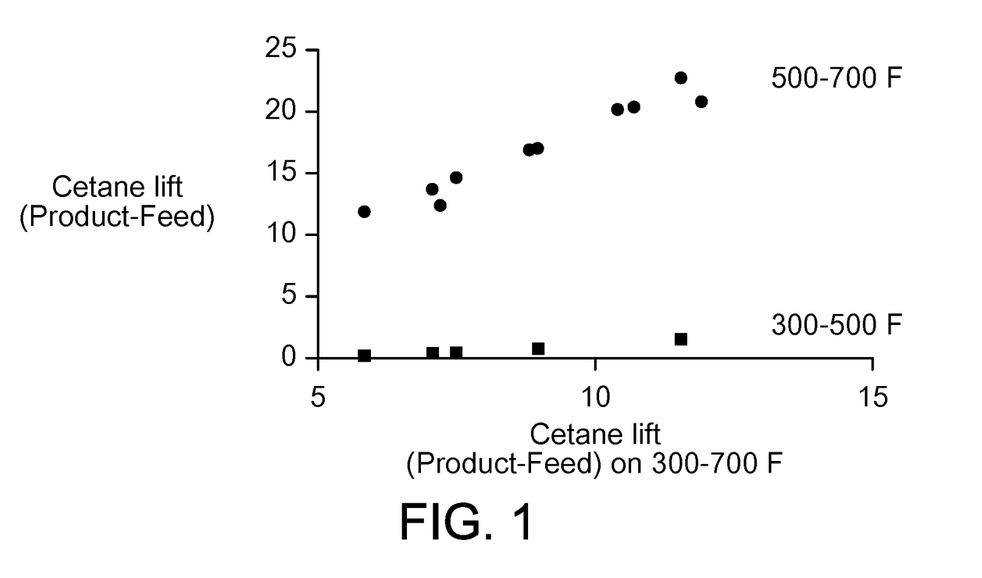
FIG. 1 is a graph showing the cetane lift at various feed boiling points.

FIG. 1 shows that when a wide range SHC product is hydrotreated, its cetane number improvement mainly comes from hydrotreating the heavier fraction of the SHC heavy diesel stream (e.g., a T5 boiling point of about 260° C. and a T95 boiling point of about 377° C. (about 500° F. to about 710° F.)). Hydrotreating the kerosene portion (e.g., a T5 boiling point of about 149° C. and a T95 boiling point of about 260° C. (about 300° F. to about 500° F.)) provides a very small contribution. Because hydrotreating the kerosene portion provides very little improvement in cetane number, it is much more economical to provide deeper hydrotreating only to the heavy diesel fraction.

Figure 2:
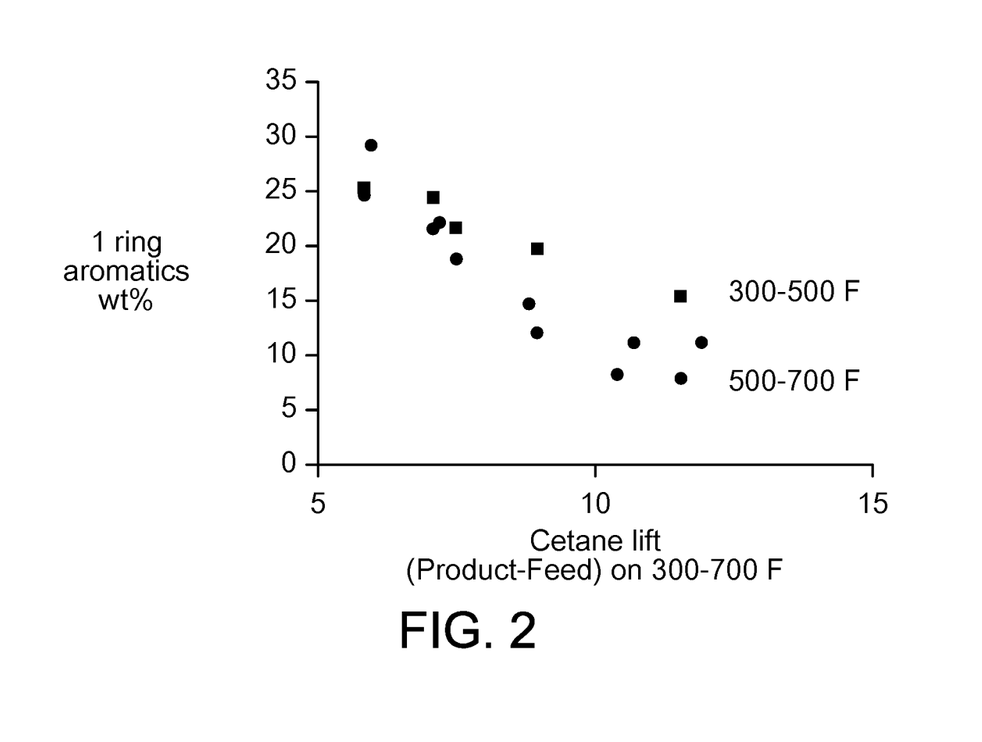
FIG. 2 is a graph showing the amount of 1 ring aromatics as a function of cetane lift for different boiling point fractions.

FIG. 2 indicates that the heavier fraction has the least amount of 1-ring aromatics. The heavier fraction also has the least amount of naphthene. Both naphthene and 1-ring aromatics set the equilibrium limit for aromatic hydrogenation. This explains the results in FIG. 1 that the heavier portion sees more upgrading. In another words, the processing conditions should be the most severe and more hydrogen should be added to the fraction that has the most potential to be upgraded, and the least upgradable portion should see the least severity. The same logic applies across the naphtha, kerosene, heavy diesel, and vacuum gas oil (VGO) range.

Consequently, processes have been developed in which more severe conditions are applied to the heavier fractions. For example, when naphtha and diesel are being co-processed, the diesel fraction undergoes more severe hydroprocessing than the naphtha fraction. In this case, the separators and fractionators can change the cut points to tailor the feed boiling points going into different hydroprocessing stages, e.g., a T5 boiling point of about 16° C. and a T95 boiling point of about 260° C. (C5 to about 500° F.), and a T5 boiling point of about 260° C. and a T95 boiling point of about 371° C. (about 500° F. to about 700° F.). These streams are then sent to different hydrotreating zones with different severity (e.g., one or more of the type of catalyst, the residence time, the temperatures etc.).

SHC heavy vacuum gas oil (HVGO) contains polyaromatic materials, and recycling it back to the SHC reactor has the benefit of adding more solubility stability. Thus, there is incentive not to hydroprocess the HVGO stream.

SHC light vacuum gas oil (LVGO), is more feasible for hydroprocessing, and it produces valuable products at the end, e.g., diesel and naphtha. There is an option to blend SHC LVGO into other VGO streams, thus integrating it into a refinery wide process. When there is a need to integrate hydroprocessing of SHC LVGO (e.g., hydrotreating with or without hydrocracking) with hydroprocessing of one or more lighter product fractions from the SHC unit, the same logic as explained above may be applied. For example, a process is designed so that the VGO (LVGO, HVGO, or a combined VGO stream) is treated more severely than the diesel or naphtha (e.g., one or more of the type of catalyst, the residence time, the temperatures, etc.). Alternatively, the VGO hydroprocessing can be integrated with the diesel/naphtha hydrotreating by sharing common fractionation and recycle gas compression systems.

The processes are arranged so that different feed streams are produced, and the hydroprocessing conditions are applied separately to achieve the best performance and best economics.

As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, "vacuum bottom" means the hydrocarbon material boiling above about 524° C. AEBP as determined by any standard gas chromatographic simulated distillation method such as ASTM D2887, D6352 or D7169, all of which are used by the petroleum industry.

As used herein, "heavy vacuum gas oil (HVGO)" means the hydrocarbon material with a T5 boiling point in the range of about 418° C. to about 458° C. and a T95 boiling point in the range of about 504° C. to about 544° C.

As used herein, "light vacuum gas oil" (LVGO) means the hydrocarbon material with a T5 boiling point in the range of about 357° C. to about 397° C. and a T95 boiling point in the range of about 418° C. to about 458° C.

As used herein, "diesel" means the hydrocarbon material with a T5 boiling point in the range of about 157° C. to about 197° C. and a T95 boiling point in the range of about 357° C. to about 397° C.

As used herein, "naphtha" means the hydrocarbon material with a T5 boiling point of about −4° C. to about 36° C. and a T95 boiling point in the range of about 157° C. to about 197° C.

As used herein, "gas" means the hydrocarbon material boiling in the range less than about −4° C. to about 36° C.

As used herein, "about" is understood to mean within 10% of the value, or within 5%, or within 1%.

Figure 3:
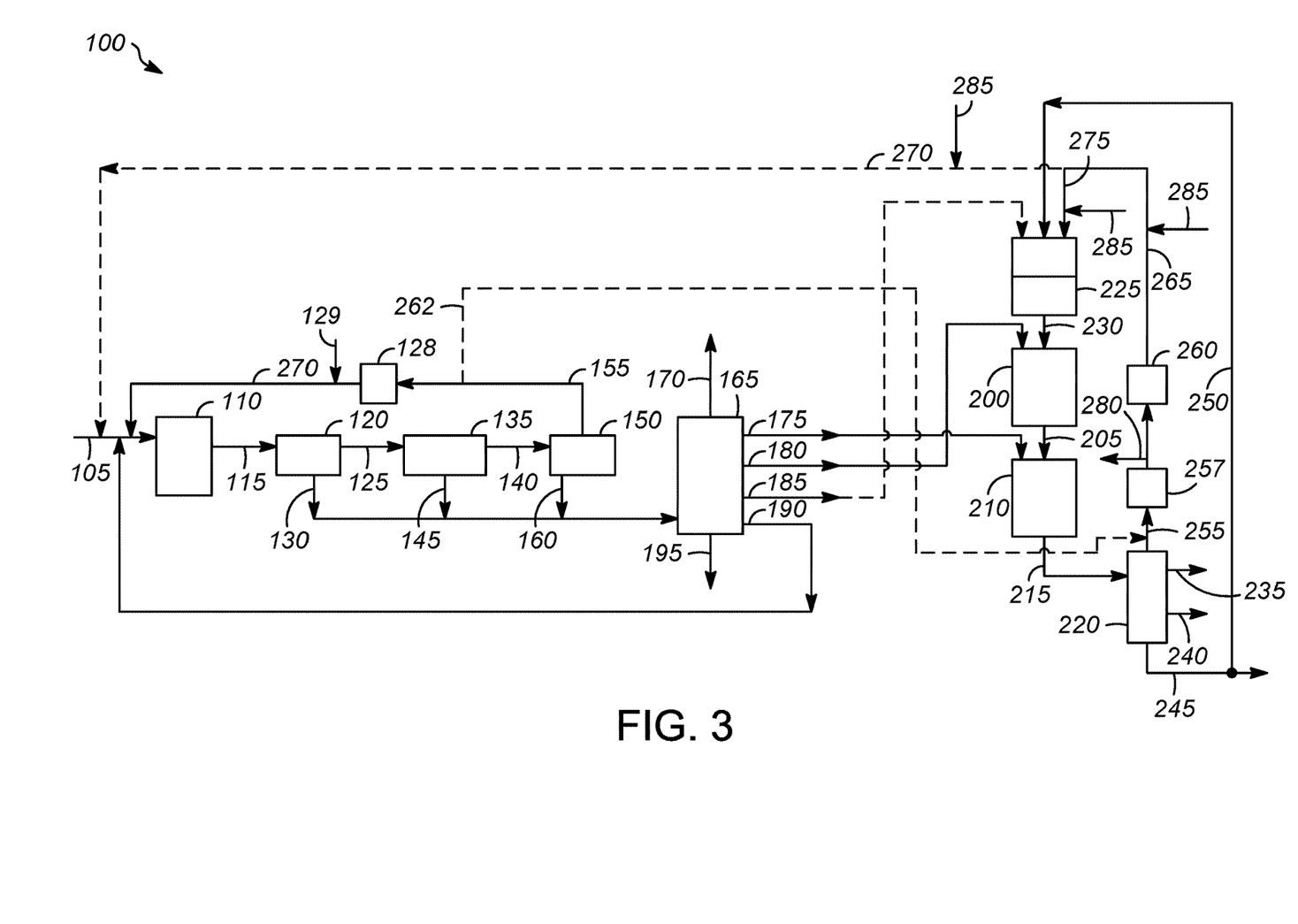
FIG. 3 is an illustration of one embodiment of the process of the present invention.

FIG. 3 illustrates one embodiment of a process 100 according to the present invention. A hydrocarbon feed 105 is introduced into a slurry hydrocracking zone 110 along with a slurry hydrocracking catalyst. Suitable hydrocarbon feeds include, but are not limited to, a vacuum column residual stream from a distillation column bottoms stream, such as with an initial boiling point from about 524+° C. (975+° F.), an atmospheric column residual stream, a visbreaker vacuum bottom stream, a fluid catalytic cracking main column bottoms stream (also called clarified slurry oil), and a solvent deasphalted oil vacuum bottoms. Other representative components, as fresh hydrocarbon feeds, that may be included in the heavy hydrocarbon feedstock include gas oils, such as straight-run gas oils (e.g., vacuum gas oil), recovered by fractional distillation of crude petroleum. Other gas oils produced in refineries include coker gas oil and visbreaker gas oil. In the case of a straight-run vacuum gas oil, the distillation end point is governed by the crude oil vacuum fractionation column and particularly the fractionation temperature cutoff between the vacuum gas oil and vacuum column bottoms split. Thus, refinery gas oil components suitable as fresh hydrocarbon feed components of the heavy hydrocarbon feedstock to the SHC reactor, such as straight-run fractions, often result from crude oil fractionation or distillation operations, while other gas oil components are obtained following one or more hydrocarbon conversion reactions. Whether or not these gas oils are present, the combined heavy hydrocarbon feedstock to the SHC reaction zone can be a mixture of hydrocarbons (i) boiling predominantly in a representative crude oil vacuum column residue range, for example above about 538° C. (1000° F.), and (ii) hydrocarbons boiling in a representative gas oil range, for example from about 343° C. (650° F.) to an end point of about 593° C. (1100° F.), with other representative distillation end points being about 566° C.

(1050° F.), about 538° C. (1000° F.), and about 482° C. (900° F.). In this case, components (i) and (ii) of the heavy hydrocarbon feedstock are therefore representative of a crude oil vacuum column residue and asphalt from a solvent deasphalting unit (also called vacuum bottom), respectively.

Additional components of the heavy hydrocarbon feed can include residual oils such as a crude oil vacuum distillation column residuum boiling above 566° C. (1050° F.), tars, bitumen, coal oils, and shale oils. Other asphaltene-containing materials such as whole or topped petroleum crude oils including heavy crude oils may also be used as components processed by SHC. In addition to asphaltenes, these further possible components of the heavy hydrocarbon feedstock, as well as others, generally also contain significant metallic contaminants (e.g., nickel, iron and vanadium), a high content of organic sulfur and nitrogen compounds, and a high Conradson carbon residue. The metals content of such components, for example, may be 100 ppm to 1,000 ppm by weight, the total sulfur content may range from 1% to 7% by weight, and the API gravity may range from about −5° to about 35°. The Conradson carbon residue of such components is generally at least about 5%, and is often from about 10% to about 35% by weight.

The hydrocarbon feed 105 entering the slurry hydrocracking zone 110 comprises three phases, solid catalyst particles, vaporous, liquid and solid hydrocarbon feed and gaseous hydrogen.

The slurry hydrocracking process can be operated at quite moderate pressure, in the range of 3.5 to 27.6 MPa (500 to 4000 psig) and preferably in the range of 10.3 to 17.2 MPa (1500 to 2800 psig), without coke formation in the slurry hydrocracking zone 110. The reactor temperature is typically in the range of about 400° C. to about 500° C., or about 410° C. to about 475° C., or 425° C. to 460° C. The liquid hourly space velocity (LHSV) is typically below about 4 $h^1$ on a fresh feed basis, with a range of about 0.1 to 3 $h^1$ being preferred and a range of about 0.1 to 1 $h^1$ being particularly preferred.

The effluent 115 from the slurry hydrocracking zone 110 is sent to a hot separator 120 where it is separated into a first vapor stream 125 and a first liquid stream 130. The hot separator 120 is operated at a temperature about in the range of about 232° C. (450° F.) to about 399° C. (750° F.), or about 232° C. (450° F.) to about 371° C. (700° F.), or about 232° C. (450° F.) to about 315° C. (650° F.), or about 371° C. (700° F.), or about 399° C. (750° F.) and a pressure in a range of about the pressure of the slurry hydrocracking zone. The first vapor stream 125 contains hydrocarbons having a T5 boiling point in the range of about −4° C. to about 36° C. and a T95 boiling point in the range of about 407° C. to about 447° C. The first liquid stream 130 contains hydrocarbons having a T5 boiling point in the range of about 129° C. to about 169° C. and a T95 boiling point beyond the measurement limit for gas chromatography (GC) simulated distillation, e.g., a T95 boiling point greater than about 518° C. to about 558° C.

In some embodiments, the first vapor stream 125 is sent to a warm separator 135 where it is separated into a second vapor stream 140 and a second liquid stream 145. The warm separator (if present) 135 is operated at a temperature between about 232° C. (450° F.) and 360° C. (680° F.), and a pressure of about the pressure of the hot separator 120.

In some embodiments, the second vapor stream 140 is sent to a cold separator 150 where it is separated into a third vapor stream 155 and a third liquid stream 160. The cold separator 150 is operated at a temperature in the range of about 20° C. (68° F.) to about 149° C. (300° F.), or about 232° C. (450° F.), and a pressure in a range of about the pressure of the hot separator 120 or warm separator 135.

The third vapor stream 155 is a hydrogen-rich stream. In some embodiments, the third vapor stream 155 is purged and then sent to the compressor 128 and merged with pure make-up stream 129 before being recycled back to slurry hydrocracking zone 110. In some embodiments, third vapor stream 155 is sent as off-gas stream 262 to merge with hydrogen-rich stream 255 as described below. In this embodiment, the compressor 128 and make-up stream 129 are not needed.

In some embodiments, there is no warm separator, and the first vapor stream 125 is sent directly to the cold separator 150.

The first, second, and third liquid streams 130, 145 (if present), and 160 are combined and sent to a first fractionation zone 165. The combined stream is fractionated into at least two streams. There could be a gas fraction 170 containing hydrocarbons having a T95 boiling point of less than about −4° C. to about 36° C., a naphtha fraction 175 containing hydrocarbons having a T5 boiling point in the range of about −4° C. to about 36° C. and a T95 boiling point in the range of about 157° C. to about 197° C., a diesel fraction 180 having a T5 boiling point in the range of about 157° C. to about 197° C. and a T95 boiling point in the range of about 357° C. to about 397° C., a light vacuum gas oil (LVGO) fraction 185 having a T5 boiling point in the range of about 357° C. to about 397° C. and a T95 boiling point in the range of about 418° C. to about 458° C., a heavy vacuum gas oil (HVGO) fraction 190 having a T5 boiling point in the range of about 418° C. to about 458° C. and a T95 boiling point in the range of about 504° C. to about 544° C., and a vacuum bottom fraction 195 having a T5 boiling point in the range of about 504° C. to about 544° C. or more and a T95 boiling point beyond the measurement limit for gas chromatography (GC) simulated distillation, e.g., a T95 boiling point greater than about 518° C. to about 558° C.

In other embodiments, more or fewer fractions could be produced. For example, in some embodiments, there could be a combined naphtha/diesel fraction having a T5 boiling point in the range of about −4° C. to about 36° C. and a T95 boiling point in the range of about 357° C. to about 397° C.

In some embodiments, the HVGO fraction 190 is recycled to the slurry hydrocracking zone 110. The vacuum bottom fraction 195 can be a side product to be further processed or utilized.

The diesel fraction 180 is sent to a first hydrotreating reactor 200. Hydrotreating is a process in which hydrogen gas is contacted with a hydrocarbon stream in the presence of suitable catalysts which are primarily active for the removal of heteroatoms, such as sulfur, nitrogen, and metals from the hydrocarbon feedstock. In hydrotreating, hydrocarbons with double and triple bonds may be saturated. Aromatics may also be saturated. Typical hydrotreating reaction conditions include a temperature of about 290° C. (550° F.) to about 455° C. (850° F.), a pressure of about 3.4 MPa (500 psig) to about 20.7 MPa (3000 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

The effluent 205 from the first hydrotreating reactor 200 and the naphtha fraction 175 are sent to a second hydrotreating reactor 210. Thus, the diesel fraction 180 is subjected to longer residence time and more severe hydrotreating than the naphtha fraction 175. Since the first and second hydrotreating reactors 200 and 210 are integrated, the total pressure is set by the limiting material fraction, i.e., diesel fraction 180. The description of diesel and naphtha are relative to their boiling point ranges. A lighter fraction and heavier fraction can be applied in a similar integration scheme following the same principle.

In some embodiments, the LVGO fraction 185 is sent to a hydrotreating and hydrocracking reactor 225. The hydrotreating and hydrocracking reactor 225 could include one or more reactors, each with one or more beds containing hydrotreating catalyst and/or hydrocracking catalyst. For example, there could be one reactor with one or more beds of hydrotreating catalyst, and one reactor with one or more beds of hydrocracking catalyst.

Hydrocracking is a process in which hydrocarbons crack in the presence of hydrogen to lower molecular weight hydrocarbons. Typical hydrocracking conditions may include a temperature of about 290° C. (550° F.) to about 468° C. (875° F.), a pressure of about 3.5 MPa (500 psig) to about 20.7 MPa (3000 psig), a LHSV of about 1.0 to less than about 2.5 $hr^{-1}$, and a hydrogen rate of about 421 to about 2,527 $Nm^3/m^3$ oil (2,500-15,000 scf/bbl). Typical hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Additional hydrogenating components may be selected from Group VIB for incorporation with the zeolite base. Hydrocracking of a VGO feed significantly reduces molecular weight and generates lower boiling point products, e.g. diesel.

The effluent 230 from the hydrotreating and hydrocracking reactor 225 is sent to the first hydrotreating reactor 200 with the diesel fraction 180. As a result, the LVGO fraction 185 experiences longer residence time and a more severe hydrotreatment than the diesel fraction 180. Since the hydrotreating and hydrocracking reactor 225 and first hydrotreating reactor 200 are integrated, the total pressure is set by the limiting material fraction, i.e., LVGO fraction 185. The description of LHSV and diesel are relative to their boiling point ranges. In the same manner, a lighter fraction and heavier fraction can be produced in the fractionation unit, and a similar integration scheme can be applied following the same principle.

The effluent 215 from the second hydrotreating reactor 210 is sent to a separation/fractionation zone 220 where it is separated into at least two product streams. The separation/fractionation zone 220 can include one or more separators, stripper columns, and/or distillation columns to recover the products in desired boiling range.

In some embodiments where the naphtha and diesel fractions 175, 180 are treated, the effluent 215 is separated into at least a naphtha product stream 235 and a diesel product stream 240. In other embodiments where the LVGO fraction 185 is also treated, there would also be an unconverted LVGO product stream 245.

In some embodiments, a portion 250 of the unconverted LVGO product stream 245 can be recycled to the hydrotreating and hydrocracking reactor 225, if desired.

A hydrogen rich stream 255 (optionally combined with the SHC off-gas stream 262) can optionally be sent to sour gas scrubber 257 and/or a purging stream 280 can be removed. It can then be sent to the compressor 260. The compressed hydrogen stream 265 can be recycled to the slurry hydrocracking zone 110 as recycle gas stream 270 or to one or more of the hydrotreating and hydrocracking reactor 225, and first and second hydrotreating reactors 200, 210 as recycle gas stream 275. Makeup hydrogen stream 285 can be added as needed to one or more of the compressed hydrogen stream 265, or recycle gas streams 270, 275, preferably the latter.

When the slurry hydrocracking zone 110 and the first and second hydrotreating reactors 200, 210 and the hydrotreating and hydrocracking reactor 225 utilize a separate recycle gas system, the pressures of the first and second hydrotreating reactors 200, 210 and the hydrotreating and hydrocracking reactor 225 are set by the hydroprocessing needs, e.g., LVGO or diesel hydroprocessing, e.g., 3.5 MPa (500 psig) to about 17.2 MPa (2500 psig). When the slurry hydrocracking zone 110 and the first and second hydrotreating reactors 200, 210 and the hydrotreating and hydrocracking reactor 225 utilize the same recycle gas system, the system pressure is set by the slurry hydrocracking zone 110.

Figure 4:
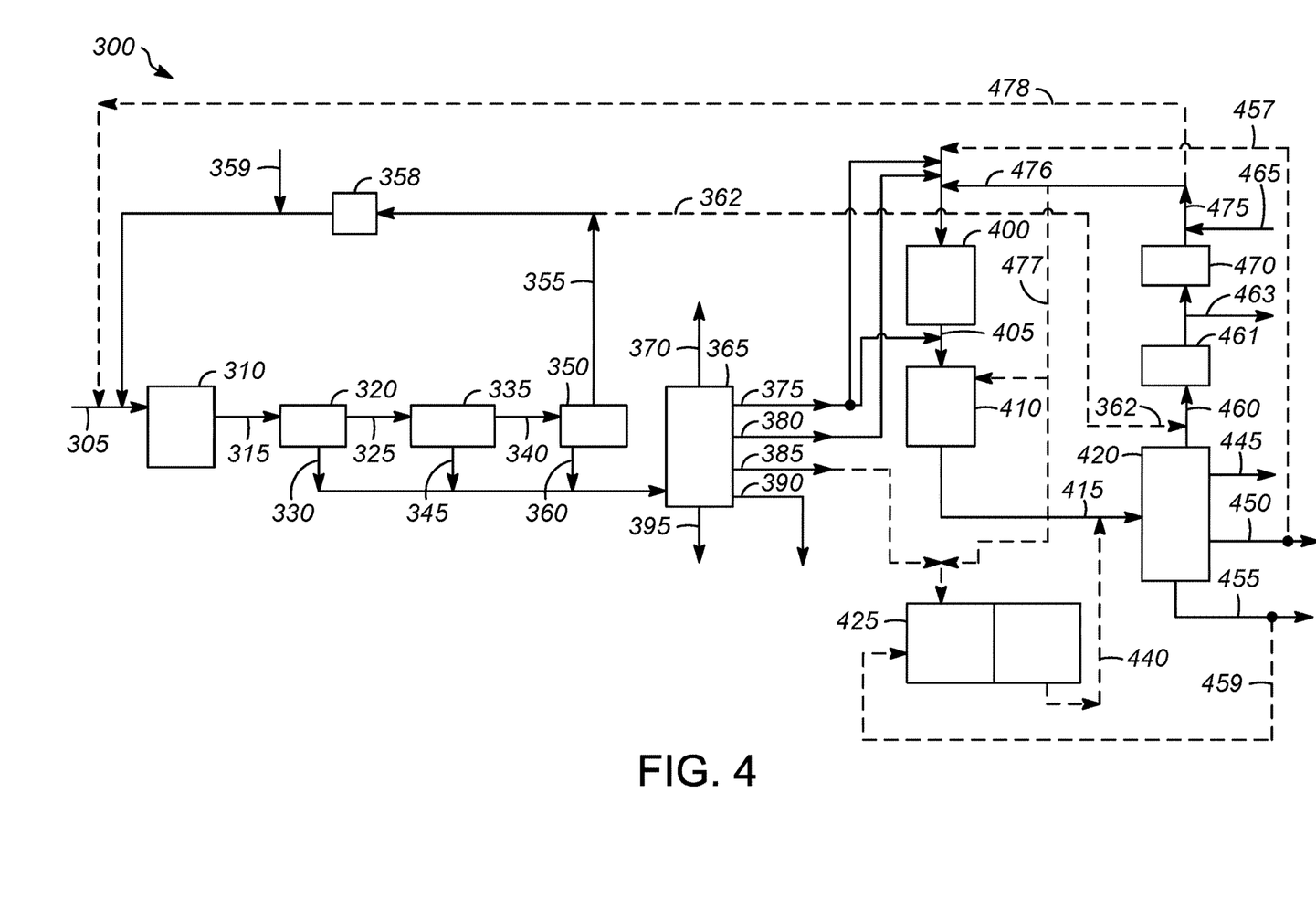
FIG. 4 is an illustration of another embodiment of the process of the present invention.

FIG. 4 illustrates another embodiment of a process 300 according to the present invention. A hydrocarbon feed 305 is introduced into a slurry hydrocracking zone 310 with a slurry hydrocracking catalyst.

The effluent 315 from the slurry hydrocracking zone 310 is sent to a hot separator 320 where it is separated into a first vapor stream 325 and a first liquid stream 330.

In some embodiments, the first vapor stream 325 is sent to a warm separator 335 where it is separated into a second vapor stream 340 and a second liquid stream 345.

In some embodiments, the second vapor stream 340 is sent to a cold separator 350 where it is separated into a third vapor stream 355 and a third liquid stream 360.

The third vapor stream 355 is a hydrogen-rich stream. In some embodiments, the third vapor stream 355 is purged sent to the compressor 358, and then merged with makeup hydrogen stream 359 before being sent back to the slurry hydrocracking zone 310. In some embodiments, the third vapor stream 355 is sent as off-gas stream 362 and merged with hydrogen-rich stream 460 as described below. In this embodiment, the compressor 358 and make-up hydrogen stream 359 are not needed.

In some embodiments, there is no warm separator, and the first vapor stream 325 is sent directly to the cold separator 350.

The first, second, and third liquid streams 330, 345 (if present), and 360 are combined and sent to a fractionation zone 365. The combined stream is fractionated into at least two streams. There could be a gas fraction 370 containing hydrocarbons having a T95 boiling point of less than about −4° C. to about 36° C., a naphtha fraction 375 containing hydrocarbons having a T5 boiling point in the range of about −4° C. to about 36° C. and a T95 boiling point in the range of about 157° C. to about 197° C., a diesel fraction 380 having a T5 boiling point in the range of about 157° C. to about 197° C. and a T95 boiling point in the range of about 357° C. to about 397° C., a LVGO fraction 385 having a T5 boiling point in the range of about 357° C. to about 397° C. and a T95 boiling point in the range of about 418° C. to about 458° C., a HVGO fraction 390 having a T5 boiling point in the range of about 418° C. to about 458° C. and a T95 boiling point in the range of about 504° C. to about 544° C., and a vacuum bottom fraction 395 having a T5 boiling point in the range of about 504° C. to about 544° C. or more, and a T95 boiling point beyond the measurement limit for gas chromatography (GC) simulated distillation, e.g., a T95 boiling point in the range of about 518° C. to about 558° C. or more. More or fewer fractions could be produced, as discussed above.

In some embodiment, the HVGO fraction 390 is recycled to the slurry hydrocracking zone 310. The vacuum bottom fraction 395 can be a side product to be further processed or utilized.

The diesel fraction 380 is sent to a first hydrotreating reactor 400. The effluent 405 from the first hydrotreating reactor 400 and the naphtha fraction 375 are sent to a second hydrotreating reactor 410. Thus, the diesel fraction 380 is subjected to more severe hydrotreating than the naphtha fraction 375.

In some embodiments, a portion or all of the naphtha fraction 375 could be sent to the first hydrotreating reactor 400.

The effluent 415 from the second hydrotreating reactor 410 is sent to a separation/fractionation zone 420 where it is separated into at least two product streams.

In some embodiments, the LVGO fraction 385 is separately sent to a hydrotreating and hydrocracking reactor 425. The effluent 440 from the hydrotreating and hydrocracking reactor 425 can be combined with the effluent 415 from the second hydrotreating reactor 410. As a result, the LVGO hydroprocessing is integrated with the diesel/naphtha hydrotreating only in the product separation/fractionation zone 420.

The effluent 415 from the second hydrotreating reactor 410 (or combined with the effluent 440, if present, from the hydrotreating and hydrocracking reactor 425 in some embodiments) is sent to the separation/fractionation zone 420. In some embodiments, the effluent 415 (and effluent 440 if present) is separated into at least a naphtha product stream 445 and a diesel product stream 450. In other embodiments, there would also be a LVGO product stream 455.

In some embodiments, a portion 457 of the diesel product stream 450 can be recycled to the first hydrotreating reactor 400, if desired. In some embodiments, a portion 459 of the LVGO product stream 455 can be recycled to the LVGO hydrotreating and hydrocracking reactor 425, if desired.

A hydrogen rich stream 460 can optionally be sent to sour gas scrubber 461 and/or a purging stream 463 can be removed. It can then be sent to the compressor 470. In some embodiments, off-gas stream 362 is merged with hydrogen-rich stream 460, purged, and sent to the compressor 470. The compressed hydrogen stream 475 is recycled to provide hydrogen requirement to one or more of the first and second hydrotreating reactors 400, 410, and hydrotreating and hydrocracking reactor 425, and in some embodiments, the slurry hydrocracking zone 310. Make-up gas stream 465 can be selectively added to compressed hydrogen stream 475, or recycle gas streams 476, 477 or 478.

Figure 5:
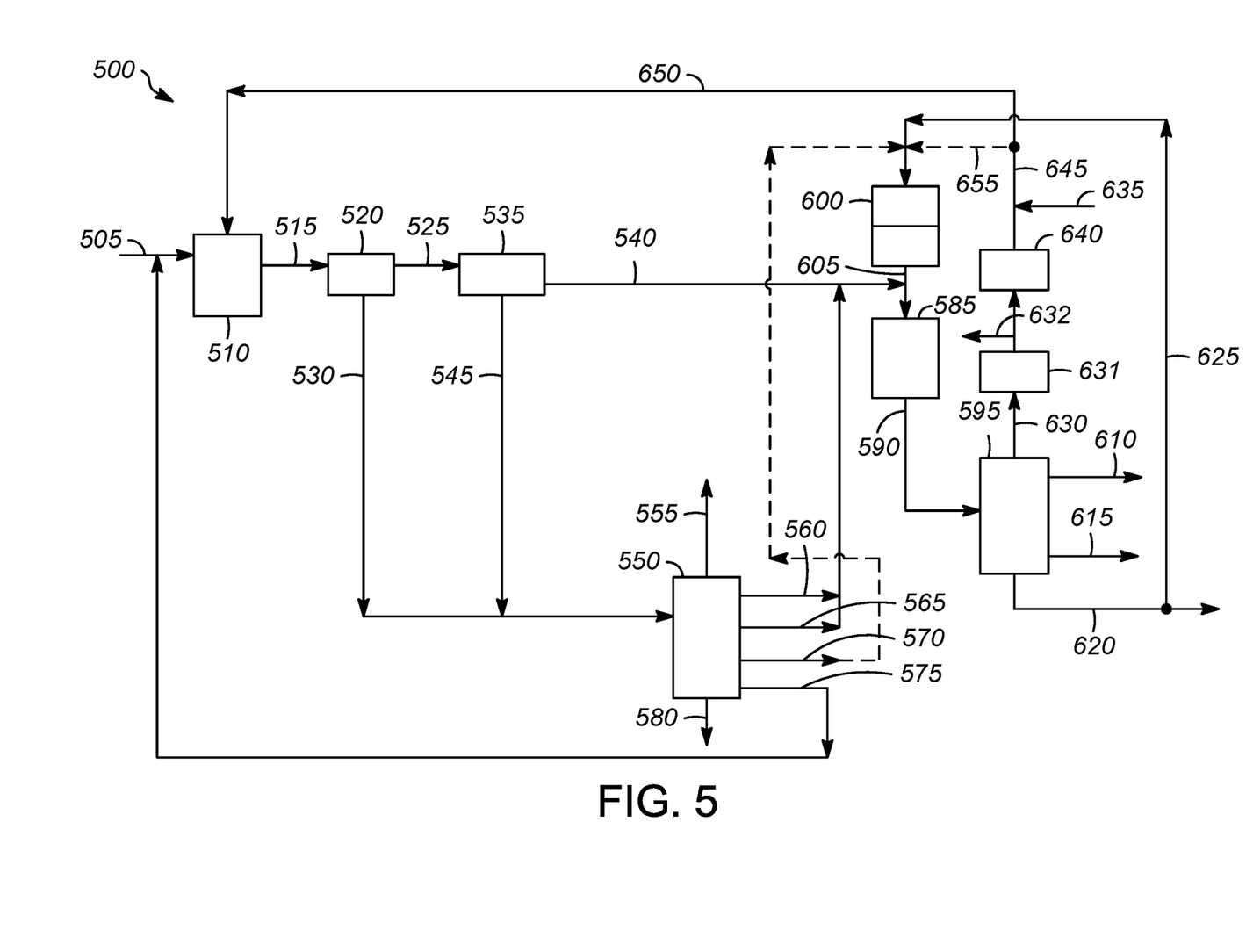
FIG. 5 is an illustration of yet another embodiment of the process of the present invention.

FIG. 5 illustrates another embodiment of a process 500 according to the present invention. A hydrocarbon feed 505 is introduced into a slurry hydrocracking zone 510 with a slurry hydrocracking catalyst.

The effluent 515 from the slurry hydrocracking zone 510 is sent to a hot separator 520 where it is separated into a first vapor stream 525 and a first liquid stream 530.

The first vapor stream 525 is sent to a warm separator 535 where it is separated into a second vapor stream 540 and a second liquid stream 545.

The first and second liquid streams 530, 545 are combined and sent to a fractionation zone 550. The combined stream is fractionated into at least two streams. There could be a gas fraction 555 containing hydrocarbons having a T95 boiling point of less than about −4° C. to about 36° C., a naphtha fraction 560 containing hydrocarbons having a T5 boiling point in the range of about −4° C. to about 36° C. and a T95 boiling point in the range of about 157° C. to about 197° C., a diesel fraction 565 having a T5 boiling point in the range of about 157° C. to about 197° C. and a T95 boiling point in the range of about 357° C. to about 397° C., a LVGO fraction 570 having a T5 boiling point in the range of about 357° C. to about 397° C. and a T95 boiling point in the range of about 418° C. to about 458° C., a HVGO fraction 575 having a T5 boiling point in the range of about 418° C. to about 458° C. and a T95 boiling point in the range of about 504° C. to about 544° C., and a vacuum bottom fraction 580 having a T5 boiling point in the range of about 504° C. to about 544° C. or more, and a T95 boiling point beyond the measurement limit for gas chromatography (GC) simulated distillation, e.g., a T95 boiling point greater than about 518° C. to about 558° C. More or fewer fractions could be produced, as discussed above.

In some embodiments, the HVGO fraction 575 is recycled to the slurry hydrocracking zone 510. The vacuum bottom fraction 580 can be a side product to be further processed or utilized.

The naphtha fraction 560 and diesel fraction 565 (or a single fraction including hydrocarbons having a T5 boiling point in the range of about −4° C. to about 36° C. and a T95 boiling point in the range of about 357° C. to about 397° C.) are combined with the second vapor stream 540 and sent to a first hydrotreating reactor 585.

The effluent 590 from the first hydrotreating reactor 585 is sent to a separation/fractionation zone 595 where it is separated into at least two product streams.

In some embodiments, the LVGO fraction 570 is sent to a hydrotreating and hydrocracking reactor 600. The effluent 605 from the hydrotreating and hydrocracking reactor 600 is sent to the first hydrotreating reactor 585.

The effluent 590 from the first hydrotreating reactor 585 is sent to the separation/fractionation zone 595. In some embodiments, the effluent 590 is separated into at least a naphtha product stream 610 and a diesel product stream 615. In other embodiments, there would also be a LVGO product stream 620. In some embodiments, a portion 625 of the LVGO product stream 620 can be recycled to the hydrotreating and hydrocracking reactor 600, if desired.

A hydrogen rich stream 630 can optionally be sent to a sour gas scrubber 631, and/or a purge stream 632 can then be removed. It can then be sent to the compressor 640. The compressed hydrogen stream 645 is merged with make-up hydrogen 635, then sent to the slurry hydrocracking zone 510. When there is a hydrotreating and hydrocracking reactor 600, the compressed hydrogen stream 645 can be split into a portion 650 to provide the hydrogen requirement to the slurry hydrocracking zone 310 and a portion 655 to provide the hydrogen requirement to the hydrotreating and hydrocracking reactor 600. In this case, make up gas can be added to either stream or both streams (not shown).

Figure 6:
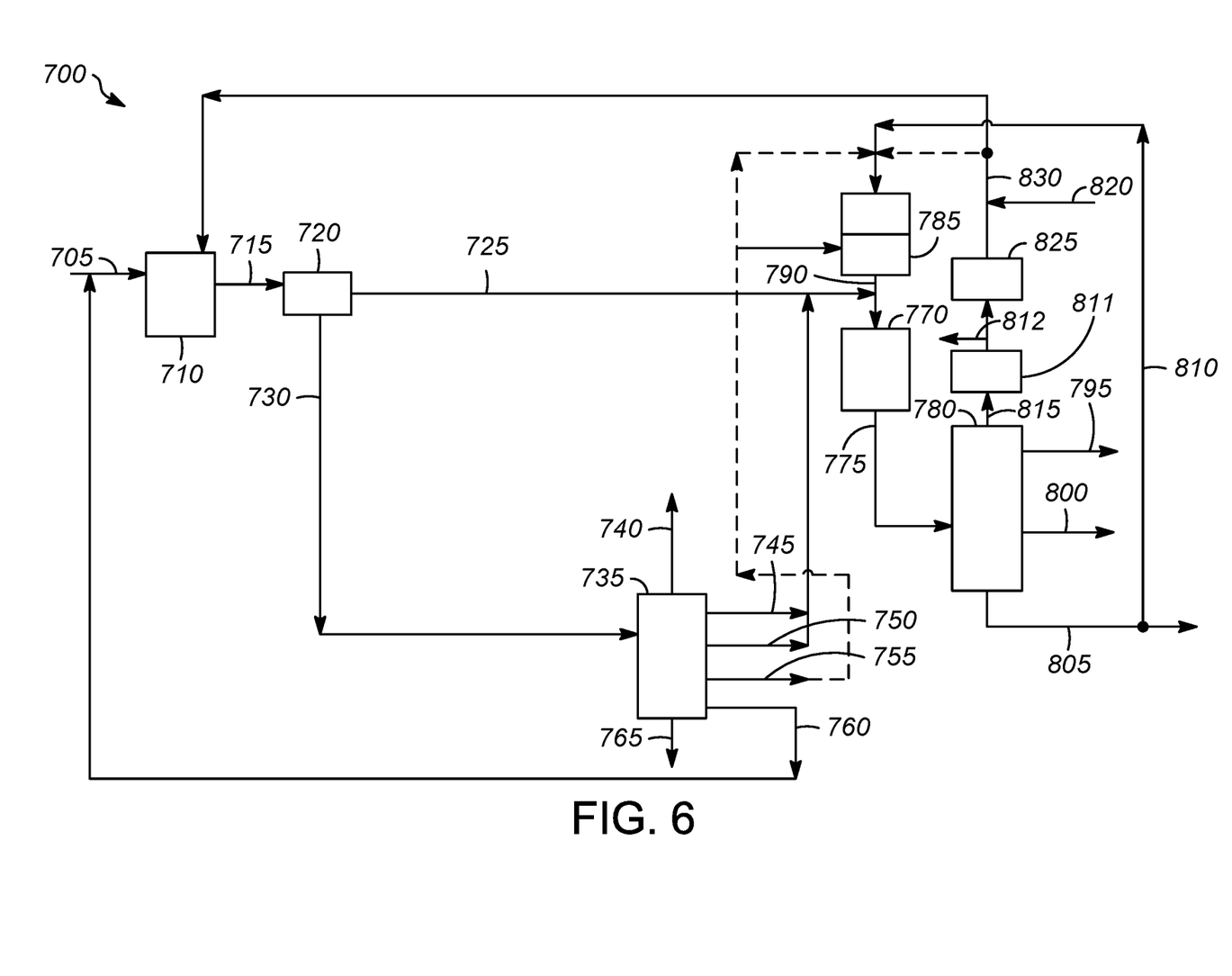
FIG. 6 is an illustration of another embodiment of the process of the present invention.

FIG. 6 illustrates another embodiment of a process 700 according to the present invention. In this embodiment, there is no warm separator.

A hydrocarbon feed 705 is introduced into a slurry hydrocracking zone 710 with a slurry hydrocracking catalyst.

The effluent 715 from the slurry hydrocracking zone 710 is sent to a hot separator 720 where it is separated into a first vapor stream 725 and a first liquid stream 730.

The first liquid stream 730 is sent to a fractionation zone 735. The combined stream is fractionated into at least two streams. There could be a gas fraction 740 containing hydrocarbons having a T95 boiling point of less than about −4° C. to about 36° C., a naphtha fraction 745 containing hydrocarbons having a T5 boiling point in the range of about −4° C. to about 36° C. and a T95 boiling point in the range of about 157° C. to about 197° C., a diesel fraction 750 having a T5 boiling point in the range of about 157° C. to about 197° C. and a T95 boiling point in the range of about 357° C. to about 397° C., a LVGO fraction 755 having a T5 boiling point in the range of about 357° C. to about 397° C. and a T95 boiling point in the range of about 418° C. to about 458° C., a HVGO fraction 760 having a T5 boiling point in the range of about 418° C. to about 458° C. and a T95 boiling point in the range of about 504° C. to about 544° C., and a vacuum bottom fraction 765 having a T5 boiling point in the range of about 504° C. to about 544° C. or more, and a T95 boiling point beyond the measurement limit for gas chromatography (GC) simulated distillation, e.g., a T95 boiling point greater than about 518° C. to about 558° C. More or fewer fractions could be produced, as discussed above.

In some embodiments, the HVGO fraction 760 is recycled to the slurry hydrocracking zone 710. The vacuum bottom fraction 765 can be a side product to be further processed or utilized.

The naphtha fraction 745 and diesel fraction 750 (or a single fraction including hydrocarbons having a T5 boiling point in the range of about −4° C. to about 36° C. and a T95 boiling point in the range of about 357° C. to about 397° C.) are combined with the first vapor stream 725 and sent to a first hydrotreating reactor 770.

The effluent 775 from the first hydrotreating reactor 770 is sent to a separation/fractionation zone 780 where it is separated into at least two product streams.

In some embodiments, the LVGO fraction 755 is sent to a hydrotreating and hydrocracking reactor 785. The effluent 790 from the hydrotreating and hydrocracking reactor 785 is sent to the first hydrotreating reactor 770.

The effluent 775 from the first hydrotreating reactor 770 is sent to the separation/fractionation zone 780. In some embodiments, the effluent 775 is separated into at least a naphtha product stream 795 and a diesel product stream 800. In other embodiments, there would also be a LVGO product stream 805. In some embodiments, a portion 810 of the LVGO product stream 805 can be recycled to the hydrotreating and hydrocracking reactor 785, if desired.

A hydrogen rich stream 815 can optionally be sent to a scrubber 811 and/or a purging stream 812 can be removed. It can then be sent to the compressor 825. The compressed hydrogen stream 830 is merged with make-up hydrogen 820 and can be recycled back to the slurry hydrocracking zone 710. In some embodiments, the compressed hydrogen stream 830 can be split and recycled to one or more of the first hydrotreating reactor 770, the hydrotreating and hydrocracking reactor 785, and the slurry hydrocracking zone 710. In this case, make up gas can be added to any of the recycle streams (not shown).

Figure 7:
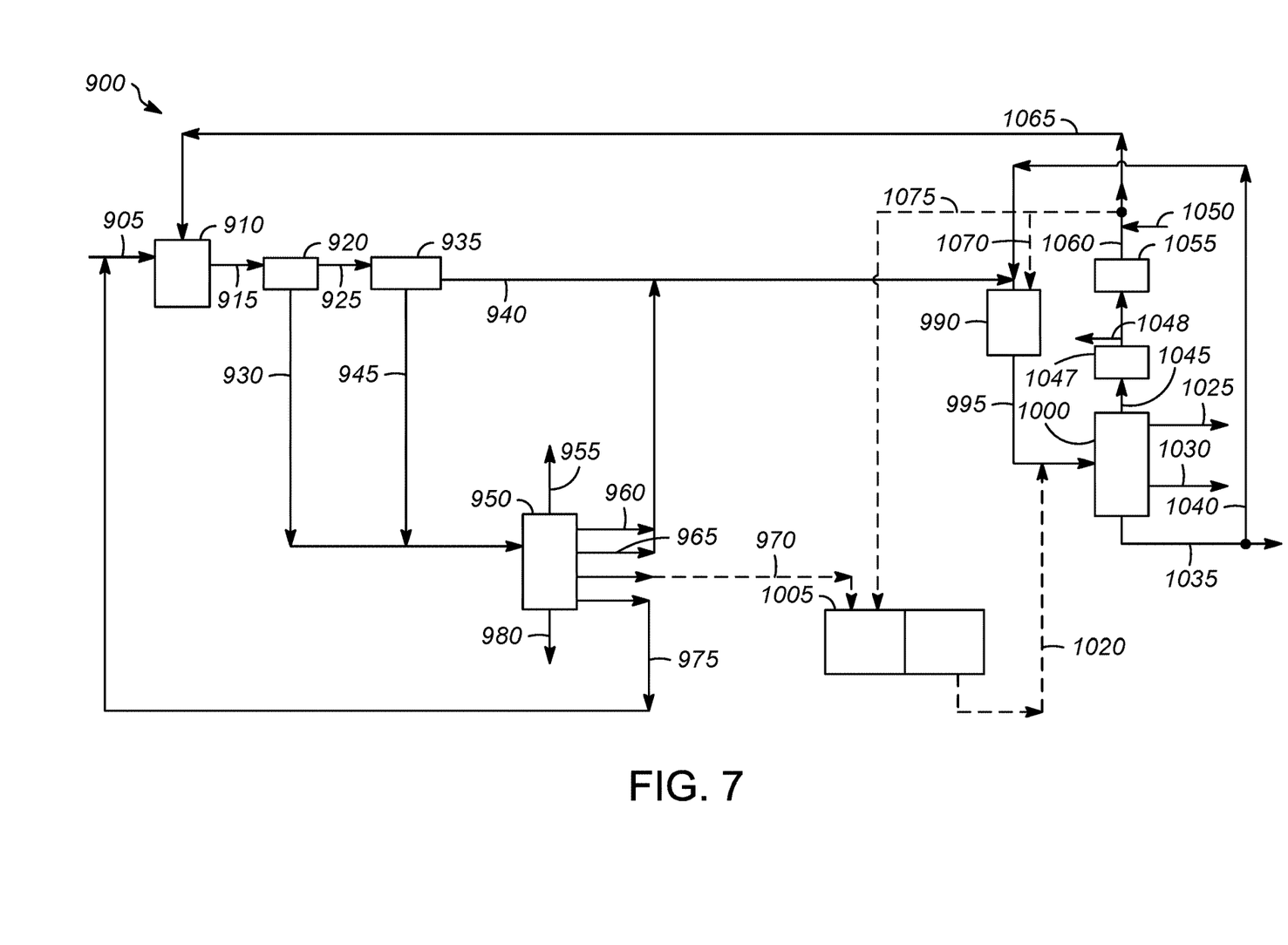
FIG. 7 is an illustration of still another embodiment of the process of the present invention.

FIG. 7 illustrates another embodiment of a process 900 according to the present invention. A hydrocarbon feed 905 is introduced into a slurry hydrocracking zone 910 with a slurry hydrocracking catalyst.

The effluent 915 from the slurry hydrocracking zone 910 is sent to a hot separator 920 where it is separated into a first vapor stream 925 and a first liquid stream 930.

In some embodiments, the first vapor stream 925 is sent to a warm separator 935 where it is separated into a second vapor stream 940 and a second liquid stream 945.

The first and second liquid streams 930, 945 are sent to a fractionation zone 950. The combined stream is fractionated into at least two streams. There could be a gas fraction 955 containing hydrocarbons having a T95 boiling point of less than about −4° C. to about 36° C., a naphtha fraction 960 containing hydrocarbons having a T5 boiling point in the range of about −4° C. to about 36° C. and a T95 boiling point in the range of about 157° C. to about 197° C., a diesel fraction 965 having a T5 boiling point in the range of about 157° C. to about 197° C. and a T95 boiling point in the range of about 357° C. to about 397° C., a LVGO fraction 970 having a T5 boiling point in the range of about 357° C. to about 397° C. and a T95 boiling point in the range of about 418° C. to about 458° C., a HVGO fraction 975 having a T5 boiling point in the range of about 418° C. to about 458° C. and a T95 boiling point in the range of about 504° C. to about 544° C., and a vacuum bottom fraction 980 having a T5 boiling point in the range of about 504° C. to about 544° C. or more, and a T95 boiling point beyond the measurement limit for gas chromatography (GC) simulated distillation, e.g., a T95 boiling point greater than about 518° C. to about 558° C. More or fewer fractions could be produced, as discussed above.

In some embodiments, the HVGO fraction 975 is recycled to the slurry hydrocracking zone 910. The vacuum bottom fraction 980 can be a side product to be further processed or utilized.

The naphtha fraction 960 and diesel fraction 965 (or a single fraction including hydrocarbons having a T5 boiling point in the range of about −4 to about 36° C. and a T95 boiling point in the range of about 357° C. to about 597° C.) are combined with the second vapor stream 940 and sent to a first hydrotreating reactor 990.

In other embodiments, the warm separator is omitted. In this case, the first liquid stream 930 is sent to the fractionation zone 950. The naphtha fraction 960 and diesel fraction 965 are combined with the first vapor stream 925 and sent to the first hydrotreating reactor 990.

The effluent 995 from the first hydrotreating reactor 990 is sent to a separation/fractionation zone 1000 where it is separated into at least two product streams.

In some embodiments, the LVGO fraction 970 is sent to a separate hydrotreating and hydrocracking reactor 1005. The effluent 1020 from the hydrotreating and hydrocracking reactor 1005 is combined with the effluent 995 from the first hydrotreating reactor 990 and sent to the common separation/fractionation zone 1000.

The effluent 995 from the first hydrotreating reactor 990 (and effluent 1020 from the hydrotreating and hydrocracking reactor 1005 if present) is sent to the separation/fractionation zone 1000. In some embodiments, the effluent 995 is separated into at least a naphtha product stream 1025 and a diesel product stream 1030. In other embodiments, there would also be a LVGO product stream 1035. In some embodiments, a portion 1040 of the LVGO product stream 1035 can be recycled to the first hydrotreating reactor 990, if desired.

A hydrogen rich stream 1045 can optionally be sent to a scrubber 1047 and/or a purging stream 1048 can be removed. It can then be sent to the compressor 1055. The compressed hydrogen stream 1060 can be merged with make-up hydrogen 1050 and recycled back to the slurry hydrocracking zone 910. In some embodiments, the compressed hydrogen stream 1060 can be split into one or more recycle streams, such as recycle stream 1065, which can be sent back to the slurry hydrocracking zone 910, recycle stream 1070, which can be sent to the first hydrotreating reactor 990, and recycle stream 1075, which can be sent to the hydrotreating and hydrocracking reactor 1005. In this case, make up hydrogen 1050 can be added to compressed hydrogen stream 1060 or any of the recycle streams 1065, 1070, 1075.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for hydrotreating an effluent from a slurry hydrocracking process comprising separating the slurry hydrocracking effluent in a hot separator into a first liquid stream and a first vapor stream; separating the first vapor stream in a second separator into a second liquid stream and a second vapor stream; fractionating the first and second liquid streams into at least two fractions in a first fractionation zone, wherein the at least two fractions comprise at least a first fraction and a second fraction, the second fraction having a T5 boiling point above the T5 boiling point of the first fraction; hydrotreating the second fraction in the presence of hydrogen and a hydrotreating catalyst in a first hydrotreating reactor to form a first hydrotreated effluent; hydrotreating the first hydrotreated effluent and the first fraction in the presence of hydrogen and a hydrotreating catalyst in a second hydrotreating reactor to form a second hydrotreated effluent; and separating the second hydrotreated effluent into at least two fractions in a separation zone, wherein the at least two fractions comprise at least a naphtha product fraction and a diesel product fraction. An embodiment of the invention is one, any or all of prior embodiments in this paragraph up through the first embodiment in this paragraph wherein the second separator is a cold separator and wherein the second vapor stream comprises a hydrogen rich stream; and further comprising recycling at least a portion of the hydrogen rich stream to a slurry hydrocracking reaction zone, or the first hydrotreating reactor, or both. An embodiment of the invention is one, any or all of prior embodiments in this paragraph up through the first embodiment in this paragraph wherein the second separator is a warm separator, and further comprising separating the second vapor stream in a cold separator into a third vapor stream and a third liquid stream; combining the third liquid stream with the first and second liquid streams; optionally recycling at least a portion of the third vapor stream to a slurry hydrocracking zone, to the first hydrotreating reactor, or both; and wherein separating the first and second liquid streams into the at least two fractions comprises separating the first, second, and third liquid streams into the at least two fractions. An embodiment of the invention is one, any or all of prior embodiments in this paragraph up through the first embodiment in this paragraph wherein the first fraction has a T5 boiling point in a range of about −4° C. to about 36° C. and a T95 boiling point in a range of about 157° C. to about 197° C., and wherein the second fraction has the T5 boiling point in a range of about 157° C. to about 197° C. and a T95 boiling point in a range of about 357° C. to about 397° C. An embodiment of the invention is one, any or all of prior embodiments in this paragraph up through the first embodiment in this paragraph wherein the first fraction has a T5 boiling point in a range of about −4° C. to about 36° C. and a T95 boiling point in a range of about 357° C. to about 397° C., and wherein the second fraction has the T5 boiling point in a range of about 357° C. to about 397° C. and a T95 boiling point in a range of about 418° C. to about 458° C. An embodiment of the invention is one, any or all of prior embodiments in this paragraph up through the first embodiment in this paragraph wherein fractionating the first and second liquid streams into the at least two fractions comprises fractionating the first and second liquid streams into at least the first fraction, the second fraction, and a third fraction, the third fraction having a boiling point above the boiling point of the second fraction; and further comprising hydrotreating and hydrocracking the third fraction in the presence of hydrogen and a hydrotreating catalyst and a hydrocracking catalyst in a hydrotreating and hydrocracking reactor to form a third hydrotreated effluent; hydrotreating the third hydrotreated effluent with the second fraction in the first hydrotreating reactor to form the first hydrotreated effluent; and wherein separating the second hydrotreated effluent into the at least two fractions comprises separating the second hydrotreated effluent into at least the naphtha product fraction, the diesel product fraction, and a vacuum gas oil product fraction. An embodiment of the invention is one, any or all of prior embodiments in this paragraph up through the first embodiment in this paragraph wherein the first fraction has a T5 boiling point in a range of about −4° C. to about 36° C. and a T95 boiling point in a range of about 157° C. to about 197° C., wherein the second fraction has the T5 boiling point in a range of about 157° C. to about 197° C. and a T95 boiling point in a range of about 357° C. to about 397, and wherein the third fraction has the T5 boiling point in a range of about 357° C. to about 397° C. and a T95 boiling point in a range of about 418° C. to about 458° C. An embodiment of the invention is one, any or all of prior embodiments in this paragraph up through the first embodiment in this paragraph, further comprising recycling a portion of the vacuum gas oil product fraction to the hydrotreating and hydrocracking reactor. An embodiment of the invention is one, any or all of prior embodiments in this paragraph up through the first embodiment in this paragraph wherein fractionating the first and second liquid streams into the at least two fractions comprises fractionating the first and second liquid streams into at least the first fraction, the second fraction, and a third fraction, the third fraction having a T5 boiling point above the T5 boiling point of the second fraction; and further comprising hydrotreating and hydrocracking the third fraction in the presence of a hydrogen and a hydrotreating catalyst and a hydrocracking catalyst in a hydrotreating and hydrocracking reactor to form a third hydrotreated effluent; combining the third hydrotreated effluent with the second hydrotreated effluent to form a combined hydrotreated effluent; and wherein separating the second hydrotreated effluent into the at least two fractions in the second fractionation zone comprises separating the combined hydrotreated effluent into at least the naphtha product fraction, the diesel product fraction, and a vacuum gas oil product fraction. An embodiment of the invention is one, any or all of prior embodiments in this paragraph up through the first embodiment in this paragraph wherein a portion of the first fraction is hydrotreated in the first hydrotreating reactor with the second fraction.

A second embodiment of the invention is a process for hydrotreating an effluent from a slurry hydrocracking process comprising separating the slurry hydrocracking effluent in a hot separator into a first liquid stream and a first vapor stream; fractionating the first liquid stream into at least two fractions in a first fractionation zone, wherein the at least two fractions comprise at least a first fraction and a second fraction, the second fraction having a T5 boiling point above the T5 boiling point of the first fraction; hydrotreating the first fraction and at least a portion of the first vapor stream in the presence of hydrogen and a hydrotreating catalyst in a first hydrotreating reactor to form a first hydrotreated effluent; and separating the first hydrotreated effluent into at least two fractions in a separation zone, wherein the at least two fractions comprise at least a naphtha product fraction and a diesel product fraction. An embodiment of the invention is one, any or all of prior embodiments in this paragraph up through the second embodiment in this paragraph further comprising hydrotreating and hydrocracking the second fraction in the presence of hydrogen and a hydrotreating catalyst and a hydrocracking catalyst in a hydrotreating and hydrocracking reactor to form a second hydrotreated effluent; hydrotreating the second hydrotreated effluent with the second fraction in the first hydrotreating reactor to form the first hydrotreated effluent; and wherein separating the second hydrotreated effluent into the at least two fractions comprises separating the second hydrotreated effluent into at least the naphtha product fraction, the diesel product fraction, and a vacuum gas oil product fraction; and optionally further comprising; recycling a portion of the vacuum gas oil fraction to the hydrotreating and hydrocracking reactor. An embodiment of the invention is one, any or all of prior embodiments in this paragraph up through the second embodiment in this paragraph wherein the first fraction has a T5 boiling point in a range of about −4° C. to about 36° C. and the T95 boiling point in a range of about 157° C. to about 197° C., and wherein the second fraction has the T5 boiling point in a range of about 157° C. to about 197° C. and the T95 boiling point in a range of about 357° C. to about 397° C. An embodiment of the invention is one, any or all of prior embodiments in this paragraph up through the second embodiment in this paragraph wherein the first fraction has a T5 boiling point of about −4° C. to about 36° C. and a T95 boiling point in a range of about 357° C. to about 397° C., and wherein the second fraction has the T5 boiling point in a range of about 357° C. to about 397° C. and a T95 boiling point in a range of about 418° C. to about 458° C. An embodiment of the invention is one, any or all of prior embodiments in this paragraph up through the second embodiment in this paragraph wherein fractionating the first liquid stream into the at least two fractions comprises fractionating the first liquid stream into at least the first fraction, the second fraction, and a third fraction, the third fraction having a T5 boiling point above the T5 boiling point of the second fraction; and further comprising hydrotreating and hydrocracking the third fraction in the presence of hydrogen and a hydrotreating catalyst and a hydrocracking catalyst in a hydrotreating and hydrocracking reactor to form a second hydrotreated effluent; hydrotreating the second hydrotreated effluent with the first fraction, the second fraction, and the at least the portion of the first vapor stream in the first hydrotreating reactor to form the first hydrotreated effluent; and wherein separating the first hydrotreated effluent into the at least two fractions comprises separating the first hydrotreated effluent into at least the naphtha product fraction, the diesel product fraction, and a vacuum gas oil product fraction; and optionally further comprising; recycling a portion of the vacuum gas oil fraction to the hydrotreating and hydrocracking reactor. An embodiment of the invention is one, any or all of prior embodiments in this paragraph up through the second embodiment in this paragraph wherein the first fraction has a T5 boiling point in a range of about −4° C. to about 3° C. and a T95 boiling point in a range of about 157° C. to about 197° C., wherein the second fraction has the T5 boiling point in a range of about 157° C. to about 197° C. and a T95 boiling point in a range of about 357° C. to about 397° C., and wherein the third fraction has the T5 boiling point in a range of about 357° C. to about 397° C. and a T95 boiling point in a range of about 418° C. to about 458° C. An embodiment of the invention is one, any or all of prior embodiments in this paragraph up through the second embodiment in this paragraph further comprising separating the first vapor stream into a second liquid stream and a second vapor stream in a warm separator; combining the second liquid stream with the first liquid stream; and wherein fractionating the first liquid stream into at least two fractions comprises fractionating the first and second liquid streams into at least two fractions; and wherein hydrotreating the first fraction and the at least the portion of the first vapor stream comprises hydrotreating the first fraction and the second vapor stream. An embodiment of the invention is one, any or all of prior embodiments in this paragraph up through the second embodiment in this paragraph further comprising hydrotreating and hydrocracking the second fraction in the presence of a hydrogen and a hydrotreating catalyst and a hydrocracking catalyst in a hydrotreating and hydrocracking reactor to form a second hydrotreated effluent; combining the second hydrotreated effluent with the first hydrotreated effluent to form a combined hydrotreated effluent; and wherein separating the first hydrotreated effluent into the at least two fractions comprises separating the combined hydrotreated effluent into at least the naphtha product fraction, the diesel product fraction, and a vacuum gas oil product fraction. An embodiment of the invention is one, any or all of prior embodiments in this paragraph up through the second embodiment in this paragraph wherein fractionating the first liquid stream into the at least two fractions comprises fractionating the first liquid stream into at least the first fraction, the second fraction, and a third fraction, the third fraction having a boiling point above the boiling point of the second fraction; further comprising hydrotreating and hydrocracking the third fraction in the presence of a hydrogen and a hydrotreating catalyst and a hydrocracking catalyst in a hydrotreating and hydrocracking reactor to form a second hydrotreated effluent; combining the second hydrotreated effluent with the first hydrotreated effluent to form a combined hydrotreated effluent; wherein hydrotreating the first fraction and the at least the portion of the first vapor stream comprises hydrotreating the first and second fractions and the at least the portion of the first vapor stream; and wherein separating the first hydrotreated effluent into the at least two fractions comprises separating the combined hydrotreated effluent into at least the naphtha product fraction, the diesel product fraction, and a vacuum gas oil product fraction.

A third embodiment of the invention is a process for hydrotreating an effluent from a slurry hydrocracking process comprising separating the slurry hydrocracking effluent in a hot separator into a first liquid stream and a first vapor stream; separating the first vapor stream in a second separator into a second liquid stream and a second vapor stream; fractionating the first and second liquid streams into at least three fractions in a first fractionation zone, wherein the at least three fractions comprise at least a naphtha fraction, a diesel fraction, and a vacuum gas oil fraction; hydrotreating and hydrocracking the vacuum gas oil fraction in the presence of hydrogen and a hydrotreating catalyst and a hydrocracking catalyst in a hydrotreating and hydrocracking reactor to form a third hydrotreated effluent; hydrotreating the third hydrotreated effluent and the diesel fraction in the presence of hydrogen and a hydrotreating catalyst in a first hydrotreating reactor to form a first hydrotreated effluent; hydrotreating the first hydrotreated effluent and the naphtha fraction in the presence of hydrogen and a hydrotreating catalyst in a second hydrotreating reactor to form a second hydrotreated effluent; and separating the second hydrotreated effluent into at least three fractions in a separation zone, wherein the at least three fractions comprise at least a naphtha product fraction, a diesel product fraction, and a vacuum gas oil product fraction.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for hydrotreating an effluent from a slurry hydrocracking process comprising:
    separating the slurry hydrocracking effluent in a first separator into a first liquid stream and a first vapor stream;
    separating the first vapor stream in a second separator second liquid stream and a second vapor stream;
    fractionating the first and second liquid streams into at least two fractions in a first fractionation zone, wherein the at least two fractions comprise at least a first fraction and a second fraction, the second fraction having a T5 boiling point above a T5 boiling point of the first fraction;
    hydrotreating the second fraction in the presence of hydrogen and a hydrotreating catalyst in a first hydrotreating reactor to form a first hydrotreated effluent;
    hydrotreating the first hydrotreated effluent and the first fraction in the presence of hydrogen and a hydrotreating catalyst in a second hydrotreating reactor to form a second hydrotreated effluent; and
    separating the second hydrotreated effluent into at least two fractions in a separation zone, wherein the at least two fractions comprise at least a naphtha product fraction and a diesel product fraction.

2. The process of claim 1 wherein the second separator is a cold separator and wherein the second vapor stream comprises a hydrogen rich stream and further comprising recycling at least a portion of the hydrogen rich stream to a slurry hydrocracking reaction zone, or the first hydrotreating reactor, or both.

3. The process of claim 1 wherein the second separator is a warm separator, and further comprising:
    separating the second vapor stream in a cold separator into a third vapor stream and a third liquid stream;
    combining the third liquid stream with the first and second liquid streams;
    optionally recycling at least a portion of the third vapor stream to a slurry, hydrocracking zone, to the first hydrotreating reactor, or both; and
    wherein separating the first and second liquid streams into the at least two fractions comprises separating the first, second, and third liquid streams into the at least two fractions.

4. The process of claim 1 wherein the first fraction has the T5 boiling point in a range of about −4° C. to about 36° C. and a T95 boiling point in a range of about 157° C. to about 197° C., and wherein the second fraction has the T5 boiling point in a range of about 157° C. to about 197° C. and a T95 boiling point in a range of about 357° C. to about 397° C.

5. The process of claim 1 wherein the first fraction has the T5 boiling point in a range of about −4° C. to about 36° C. and a T95 boiling point in a range of about 357° C. to about 397° C., and wherein the second fraction has the T5 boiling point in a range of about 357° C. to about 397° C. and a T95 boiling point in a range of about 418° C. to about 458° C.

6. The process of claim 1 wherein fractionating the first and second liquid streams into the at least two fractions comprises fractionating the first and second liquid streams into at least the first fraction, the second fraction, and a third fraction, the third fraction having a T5 boiling point above the T5 boiling point of the second fraction; and further comprising:
    hydrotreating and hydrocracking the third fraction in the presence of hydrogen and a hydrotreating catalyst and a hydrocracking catalyst in a hydrotreating and hydrocracking reactor to form a third hydrotreated effluent;
    hydrotreating the third hydrotreated effluent with the second fraction in the first hydrotreating reactor to form the first hydrotreated effluent; and
    wherein separating the second hydrotreated effluent into the at least two fractions comprises separating the second hydrotreated effluent into at least the naphtha product fraction, the diesel product fraction, and a vacuum gas oil product fraction.

7. The process of claim 6 wherein the first fraction has the T5 boiling point in a range of about −4° C. to about 36° C. and a T95 boiling point in a range of about 157° C. to about 197° C., wherein the second fraction has the T5 boiling point in a range of about 157° C. to about 197° C. and a T95 boiling point in a range of about 357° C. to about 397, and wherein the third fraction has the T5 boiling point in a range of about 357° C. to about 397° C. and a T95 boiling point in a range of about 418° C. to about 458° C.

8. The process of claim 6, further comprising recycling a portion of the vacuum gas oil product fraction to the hydrotreating and hydrocracking reactor.

9. The process of claim 1 wherein fractionating the first and second liquid streams into the at least two fractions comprises fractionating the first and second liquid streams into at least the first fraction, the second fraction, and a third fraction, the third fraction having a boiling point above the boiling point of the second fraction; and further comprising:

hydrotreating and hydrocracking the third fraction in the presence of a hydrogen and a hydrotreating catalyst and a hydrocracking catalyst in a hydrotreating and hydrocracking reactor to form a third hydrotreated effluent;

combining the third hydrotreated effluent with the second hydrotreated effluent to form a combined hydrotreated effluent; and wherein separating the second hydrotreated effluent into the at least two fractions in the second fractionation zone comprises separating the combined hydrotreated effluent into at least the naphtha product fraction, the diesel product fraction, and a vacuum gas oil product fraction.

10. The process of claim 1 wherein a portion of the first fraction is hydrotreated in the first hydrotreating reactor with the second fraction.

11. A process for hydrotreating an effluent from a slurry hydrocracking process comprising:

separating the slurry hydrocracking effluent in a hot separator into a first liquid stream and a first vapor stream;

fractionating the first liquid stream into at least two fractions in a first fractionation zone, wherein the at least two fractions comprise at least a first fraction and a second fraction, the second fraction having a T5 boiling point above a T5 boiling point of the first fraction;

hydrotreating the first fraction and at least a portion of the first vapor stream in the presence of hydrogen and a hydrotreating catalyst in a first hydrotreating reactor to form a first hydrotreated effluent; and separating the first hydrotreated effluent into at least two fractions in a separation zone, wherein the at least two fractions comprise at least a naphtha product fraction and a diesel product fraction.

12. The process of claim 11 further comprising:

hydrotreating and hydrocracking the second fraction in the presence of hydrogen and a hydrotreating catalyst and a hydrocracking catalyst in a hydrotreating and hydrocracking reactor to form a second hydrotreated effluent;

hydrotreating the second hydrotreated effluent with the second fraction in the irst hydrotreating reactor to form the first hydrotreated effluent;

wherein separating the second hydrotreated effluent into the at least two fractions comprises separating the second hydrotreated effluent into at least the naphtha product fraction, the diesel product fraction, and a vacuum gas oil product fraction.

13. The process of claim 11 wherein the first fraction has the T5 boiling point in a range of about −4° C. to about 36° C. and the T95 boiling point in a range of about 157° C. to about 197° C., and wherein the second fraction has the T5 boiling point in a range of about 157° C. to about 197° C. and the T95 boiling point in a range of about 357° C. to about 397° C.

14. The process of claim 11 wherein the first fraction has the T5 boiling point of about −4° C. to about 36° C. and a T95 boiling point in a range of about 357° C. to about 397° C., and wherein the second fraction has the T5 boiling point in a range of about 357° C. to about 397° C. and a T95 boiling point in a range of about 418° C. to about 458° C.

15. The process of claim 11 wherein fractionating the first liquid stream into the at least two fractions comprises fractionating the first liquid stream into at least the first fraction, the second fraction, and a third fraction, the third fraction having a T5 boiling point above the T5 boiling point of the second fraction; and further comprising:

hydrotreating and hydrocracking the third fraction in the presence of hydrogen and a hydrotreating catalyst and a hydrocracking catalyst in a hydrotreating and hydrocracking reactor to form a second hydrotreated effluent;

hydrotreating the second hydrotreated effluent with the first fraction, the second fraction, and the at least the portion of the first vapor stream in the first hydrotreating reactor to form the first hydrotreated effluent;

wherein separating the first hydrotreated effluent into the at least two fractions comprises separating the first hydrotreated effluent into at least the naphtha product fraction, the diesel product fraction, and a vacuum gas oil product fraction; and optionally further comprising;

recycling a portion of the vacuum gas oil fraction to the hydrotreating and hydrocracking reactor.

16. The process of claim 15 wherein the first fraction has the T5 boiling point in a range of about −4° C. to about 3° C. and a T95 boiling point in a range of about 157° C. to about 197° C., wherein the second fraction has the T5 boiling point in a range of about 157° C. to about 197° C. and a T95 boiling point in a range of about 357° C. to about 397° C., and wherein the third fraction has the T5 boiling point in a range of about 357° C. to about 397° C. and a T95 boiling point in a range of about 418° C. to about 458° C.

17. The process of claim 11 further comprising:

separating the first vapor stream into a second liquid stream and a second vapor stream in a warm separator;

combining the second liquid stream with the first liquid stream; and wherein fractionating the first liquid stream into at least two fractions comprises fractionating the first and second liquid streams into at least two fractions; and wherein hydrotreating the first fraction and the at least the portion of the first vapor stream comprises hydrotreating the first fraction and the second vapor stream.

18. The process of claim 17 further comprising:

hydrotreating and hydrocracking the second fraction in the presence of a hydrogen and a hydrotreating catalyst and a hydrocracking catalyst in a hydrotreating and hydrocracking reactor to form a second hydrotreated effluent;

combining the second hydrotreated effluent with the first hydrotreated effluent to form a combined hydrotreated effluent; and wherein separating the first hydrotreated effluent into the at least two fractions comprises separating the combined hydrotreated effluent into at least the naphtha product fraction, the diesel product fraction, and a vacuum gas oil product fraction.

19. The process of claim 11 wherein fractionating the first liquid stream into the at least two fractions comprises fractionating the first liquid stream into at least the first fraction, the second fraction, and a third fraction, the third fraction having a boiling point above the boiling point of the second fraction; further comprising:

hydrotreating and hydrocracking the third fraction in the presence of a hydrogen and a hydrotreating catalyst and a hydrocracking catalyst in a hydrotreating and hydrocracking reactor to form a second hydrotreated effluent;

combining the second hydrotreated effluent with the first hydrotreated effluent to form a combined hydrotreated effluent;

wherein hydrotreating the first fraction and the at least the portion of the first vapor stream comprises hydrotreating the first and second fractions and the at least the portion of the first vapor stream; and wherein separating the first hydrotreated effluent into the at least two fractions comprises separating the combined hydrotreated effluent into at least the naphtha product fraction, the diesel product fraction, and a vacuum gas oil product fraction.

20. A process for hydrotreating an effluent from a slurry hydrocracking process comprising:

separating the slurry hydrocracking effluent in a hot separator into a first liquid stream and a first vapor stream;

separating the first vapor stream in a second separator into a second liquid stream and a second vapor stream;

fractionating the first and second liquid streams into at least three fractions in a first fractionation zone; wherein the at least three fractions comprise at least a naphtha fraction, a diesel fraction, and a vacuum gas oil fraction;

hydrotreating and hydrocracking the vacuum gas oil fraction in the presence of hydrogen and a hydrotreating catalyst and a hydrocracking catalyst in a hydrotreating and hydrocracking reactor to form a third hydrotreated effluent;

hydrotreating the third hydrotreated effluent and the diesel fraction in the presence of hydrogen and a hydrotreating catalyst in a first hydrotreating reactor to form a first hydrotreated effluent;

hydrotreating the first hydrotreated effluent and the naphtha fraction in the presence of hydrogen and a hydrotreating catalyst in a second hydrotreating reactor to form a second hydrotreated effluent; and separating the second hydrotreated effluent into at least three fractions in a separation zone, wherein the at least three fractions comprise at least a naphtha product fraction, a diesel product fraction, and a vacuum gas oil product fraction.

* * * * *